(12) United States Patent
Hixson

(10) Patent No.: US 7,196,628 B2
(45) Date of Patent: Mar. 27, 2007

(54) VITAL SIGNS MONITORING SYSTEM FOR ANIMALS

(75) Inventor: Tom Hixson, 25704 E. lakeview, Yale, OK (US) 74085

(73) Assignee: Tom Hixson, Yale, OK (US)

( * ) Notice: Subject to any disclaimer, the term of this patent is extended or adjusted under 35 U.S.C. 154(b) by 0 days.

(21) Appl. No.: 09/837,221

(22) Filed: Apr. 19, 2001

(65) Prior Publication Data

US 2002/0154015 A1 Oct. 24, 2002

(Under 37 CFR 1.47)

(51) Int. Cl.
G08B 23/00 (2006.01)

(52) U.S. Cl. ............... 340/573.1; 340/539; 340/870.16; 340/870.17; 340/870.09; 128/899; 128/903

(58) Field of Classification Search ................. 340/573, 340/573.1, 539, 870.16, 870.17, 870.09; 128/899, 903
See application file for complete search history.

(56) References Cited

U.S. PATENT DOCUMENTS

| | | | | | |
|---|---|---|---|---|---|
| 4,865,044 | A | * | 9/1989 | Wallace et al. | 340/573 |
| 5,559,497 | A | * | 9/1996 | Hong | 340/573 |
| 5,818,354 | A | * | 10/1998 | Gentry | 340/573 |
| 5,868,100 | A | * | 2/1999 | Marsh | 340/573 |

* cited by examiner

*Primary Examiner*—Daniel J. Wu
*Assistant Examiner*—Hung Nguyen

(57) ABSTRACT

A self powered monitoring device for monitoring an animal's temperature and other vital signs. The device may be mounted in the animal's ear, under the animals skin, or in any location which can be used to generate a reliable indication of the animals temperature and other vital signs. The temperature probe for the device is inserted subcutaneously and thermally and/or electrically connected to the housing of the device. Power for the device is provided by a miniature array of solar cells, the power from the solar cells being used to drive digital circuitry which processes signals from the various probes used to gather data concerning the animal's vital signs. The size of the array is chosen to be commensurate with the number of vital signs monitored, with the amount of sunlight, density of herd, and other factors being considered to ensure sufficient power for the device.

4 Claims, 3 Drawing Sheets

VITAL SIGNS MONITORING SYSTEM FOR ANIMALS

BACKGROUND OF THE INVENTION

The present invention relates to animal husbandry. More particularly, the invention relates to a self powered monitoring device for measuring and displaying an animal's temperature and other vital signs.

Statement of the Prior Art

With the proliferation of modem digital electronics, many of the problems of caring for large herds of livestock have been addressed. A particular problem in caring for livestock, particularly livestock maintained in large herds in corrals, cattle pens and feed lots, is the detection of a sick animal at an early stage of illness. In the past, detection was generally accomplished by visual observation of the herd, in which case the ability and attentiveness of the individual observing the herd was important as sick animals at an early stage of illness can have very minor symptoms, not easily discerned by an inexperienced or inattentive individual. More importantly, viruses contracted by the animal will spread and multiply in the animal's body so quickly, that by the time the first symptoms appear, it is too late for medication and ultimately the animal will die because of lack of early detection. For most illnesses, early detection can only be accomplished by detection of a fever, an elevated body temperature of the animal. Often, the sick animal is not detected until it begins to exhibit obvious signs of illness. By this time, the sick animal has exposed other animals in the close proximity of the herd possibly spreading the disease to others, with the result being a substantial financial loss for the owners of the herd.

And more importantly in today's animal health, viruses contracted by the animal will spread and multiply in the animal's body so quickly, that by the time the first symptom appears, it is too late for the medication and ultimately the animal will die because of lack of early detection. This early detection can only be accomplished by measuring the animal's fever. Visual early detection of the animal's fever is thus an important part of herd monitoring.

As a result of the problems of early detection of disease solely by visual observation, various sensing devices have been provided in the prior art. These devices, which include temperature monitors are helpful for determining a diseased condition in an animal at an early stage and may also be used for indicating estrus in certain domestic animals. Generally these devices measure a physiological condition such as temperature which is indicative of the health or other condition of the animal.

U.S. Pat. No. 3,070,773 issued to Woolston, et al. describes a device which transmits ambient temperature information as well as internal temperature information using a frequency-modulation technique. The described device, although useful in circumstances such as those for which the present invention is designed, requires an uneconomical, large amount of power because it is always powered up and active when an individual signal such as the internal temperature signal is present. It must be supplied with batteries which, due to the relatively large power consumption of the device, have to be replaced fairly frequently. The replacement of these batteries is a time consuming and expensive undertaking, especially for very large herds.

None of the above inventions and patents, taken either singly or in combination, is seen to describe the instant invention as claimed.

SUMMARY OF THE INVENTION

The present invention provides a self powered monitoring device for monitoring an animal's temperature and other vital signs. The device may be mounted in the animal's ear, under the animals skin, or in any location which can be used to generate a reliable indication of the animals temperature and other vital signs. The temperature probe for the device is inserted subcutaneously and thermally and/or electrically connected to the housing of the device. Power for the device is provided by a miniature array of solar cells, the power from the solar cells being used to drive digital circuitry which processes signals from the various probes used to gather data concerning the animal's vital signs. The size of the array is chosen to be commensurate with the number of vital signs monitored, with the amount of sunlight, density of herd, and other factors being considered to ensure sufficient power for the device. The solar panel would be backed up by a power source such as a battery or other electrical energy storage device. Preferably, the power source would be charged by the solar cell array.

Accordingly, it is a principal object of the invention to provide a new and improved animal monitoring device.

It is another object of the invention to provide a new and improved animal monitoring device which is self powered.

It is another object of the invention to provide a new and improved animal monitoring device which uses solar cells to generate power to operate its circuitry.

It is another object of the invention to provide a new and improved animal monitoring device which monitors the temperature of animal.

It is another object of the invention to provide a new and improved animal monitoring device which monitors other vital signs of an animal.

It is another object of the invention to provide a new and improved animal monitoring device which includes a transmitter for transmitting the vital signs of a plurality of animals to a single control and monitoring center.

It is another object of the invention to provide an early visual display of an animal's temperature in the event of a fever.

It is another object of the invention to provide a new and improved animal monitoring device which monitors and visually displays the vital signs of an animal.

Finally, it is a general object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
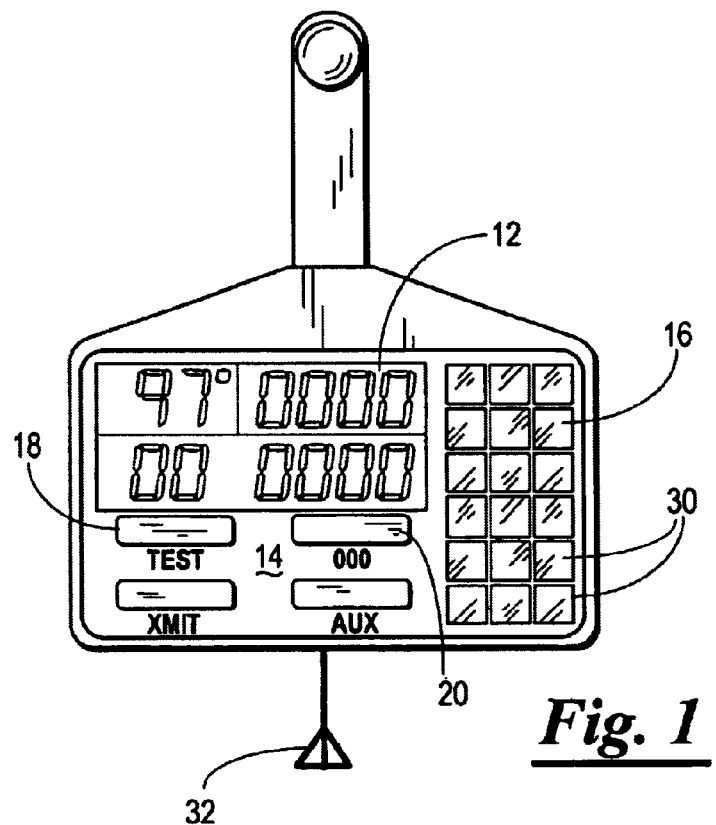
FIG. 1 shows a plan view of an exemplary front panel of an animal monitoring device in accordance with the present invention.
Figure 2:
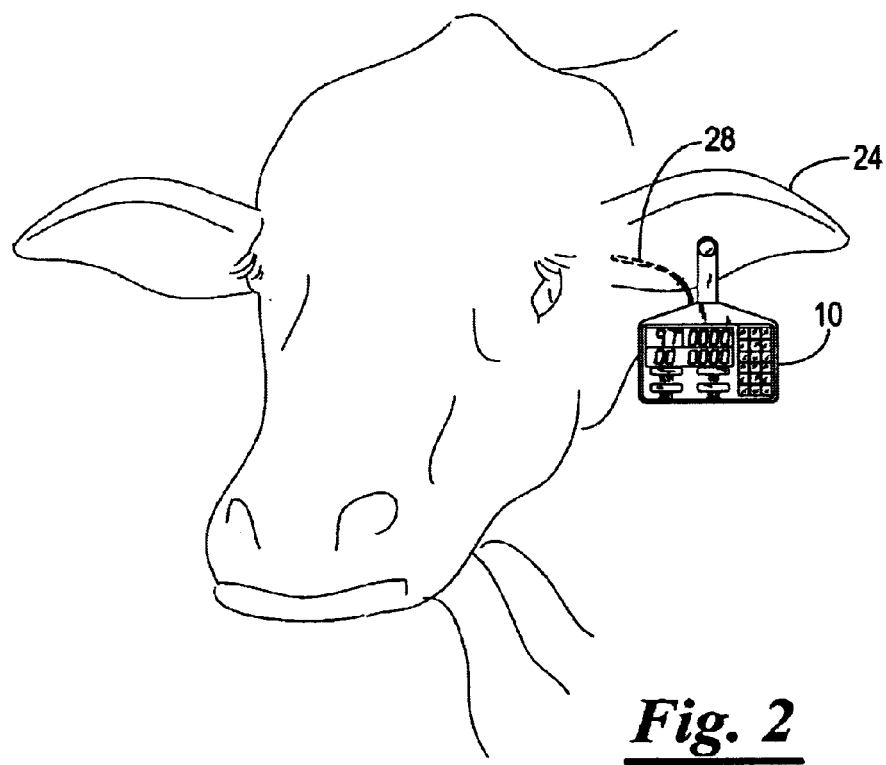
FIG. 2 shows an isometric view of the device of the present invention attached to the ear of a cow.

Referring now to FIGS. 1–4, the animal monitoring device of the invention, generally indicated by the numeral 10, is shown. The device 10 has three main components; the display panel 12, the keypad 14, and the solar cell panel 16.

The display panel 12 may be an LCD display capable of displaying at least two arabic numerals. The display panel 12 may indicate temperature, or may provides data related to other vital signs. As discussed above, it is often useful in the maintenance of livestock to detect when one or more animals in the herd have developed an illness in order to treat and/or remove them from the herd and reduce the possibility of contagion. One way of determining when an animal is ill is the presence of a fever which will appear in the animal after initial exposure to the virus or bacteria causing the infection.

For instance, if the livestock is cattle, an internal temperature of 40.degree. C. or 104.degree. F. indicates a fever and illness. For relatively small herds, daily visual inspection of the display panel 16 would be sufficient to help reduce the possibility of an infection spreading. For large herds, a transmitter for transmitting vital sign data to a central location would be advantageous.

The keypad 14 has a plurality of keys for initiating various device 10 functions. A test key 18 may function to cause the voltage generated by the solar panel 16 to be displayed. If there is insufficient voltage for the device 10 to operate the display 12 may show all zeros, blinking zeros, or be blank. Pressing the test key twice, or in combination with the 000 key 20 may cause the device to reset to zero, and reinitiate measuring the various vital signs thereby allowing the user to determine if the display 12 is displaying a current reading.

The device 10 is relatively small, approximately 3"×3" depending on the size of the solar panel 16, and is attached to the animal's ear 24 as if it were an earring, being small enough not to distract the animal or cause problems. The device 10 includes a probe 28 extending into the internal ear for exposure to the internal body temperature of the animal. An additional probe or probes, not specifically shown, may be employed to measure or derive data associated with other vital signs such as pulse rate. The probes may be inserted subcutaneously so as to be effective for their intended purposes.

Solar panel 16 has an array of solar cells 30 thereon, with a sufficient number of cells 30 to power the device 10 at least during the daylight hours. As the herd is typically only monitored during the daylight hours, 24 hour power is not needed. In accordance with one aspect of the invention, the minimum number of cells 30 needed to power the device 10 for its intended function is employed. Thus the size of the device 10 can be reduced according to the number and complexity of functions it performs.

In addition to monitoring and displaying vital signs, the device 10 may include a transmitter for transmitting, automatically at predetermined intervals, the vital signs to a central location thereby eliminating the need for visual observation. Additional solar cells 30 would be needed for this function. A transmitting antenna 32 would be coupled to the transmitter for radiating the signal. In a preferred embodiment a G.P.S. receiver/transmitter is included in the device to allow for determination of the exact location of the animal.

Figure 3:
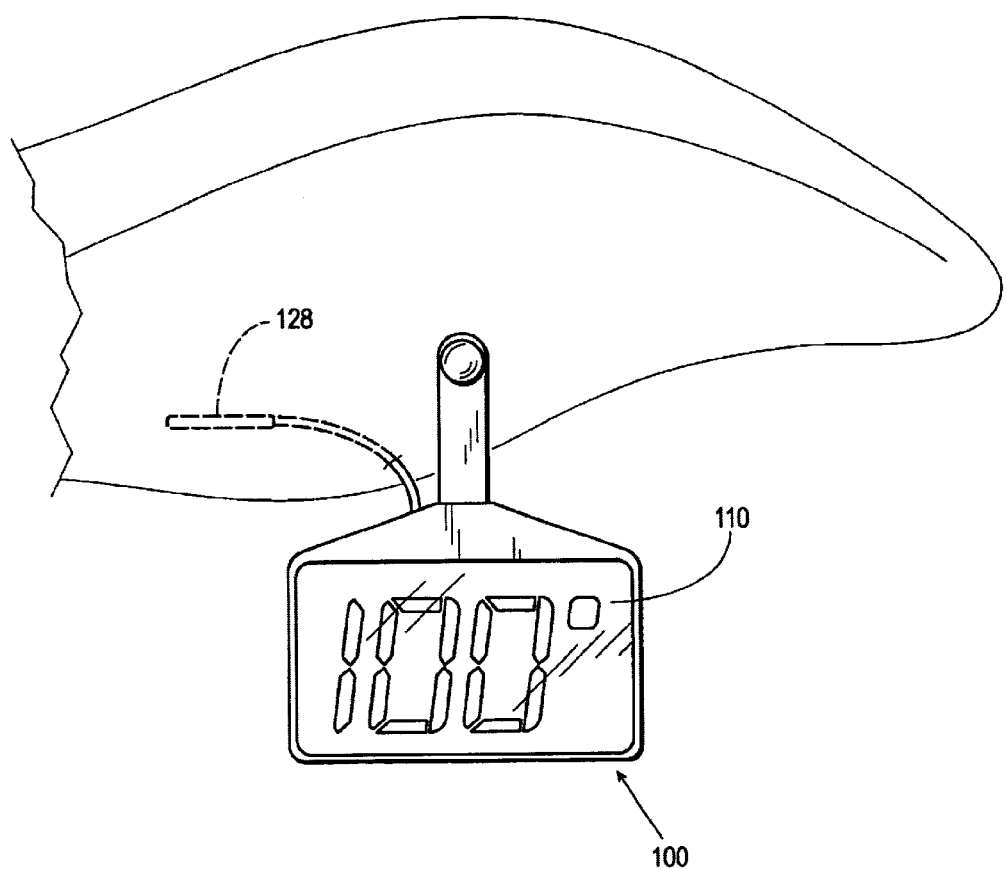
FIG. 3 shows a front plan view of an alternative configuration for an animal monitoring device made in accordance with the principles of the invention.
Figure 4:
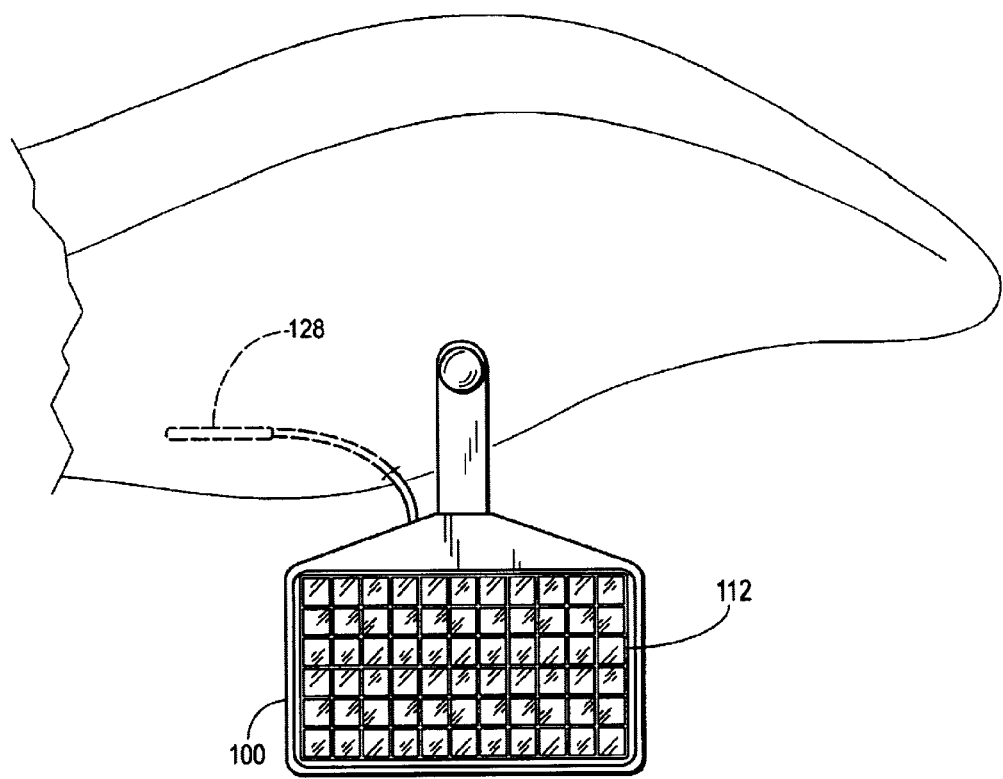
FIG. 4 shows a rear plan view of an alternative configuration for an animal monitoring device made in accordance with the principles of the invention.

Referring particularly to FIGS. 3 and 4, an alternative configuration, generally indicated by the number 100, of the animal monitoring device is shown. In this embodiment the temperature display 110 is relatively large and may be seen from a distance. The solar panel 112 is disposed on the opposite side to minimize the overall size of the device 100. A probe 128 is provided for insertion into the ear of the animal. Preferably, the visual display 110 will be visible when an animal begins to have a temperature.

In operation, the device 10, 100 is placed upon the animal as noted. When the animal's temperature exceeds a predetermined minimum, the display 12, 110 is brightly illuminated and the transmitter is activated to transmit a warning signal.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

What is claimed is:

1. An animal monitoring device comprising:

a display, said displaying capable of displaying one or more vital signs associated with the animal;

a keypad for effecting various device functions;

a solar cell array for providing power to the device, said power serving to operate circuitry for generating data corresponding to said vital signs;

wherein the size of said solar array is proportional to the number of functions said circuitry performs.

2. The device of claim 1 wherein said display is illuminated when the animal's temperature exceeds a predetermined limit.

3. The device of claim 1 wherein a transmitter powered by said solar cell array is activated when the animal's temperature exceeds a predetermined limit.

4. The device of claim 1 wherein a G.P.S. transmitter/receiver is used to allow for determination of the position of the animal.

* * * * *